US012678332B2

(12) United States Patent
Bor

(10) Patent No.: US 12,678,332 B2
(45) Date of Patent: Jul. 14, 2026

(54) SURGICAL CONTACT LENS SYSTEM WITH A PATIENT CONTACT LENS

(71) Applicant: Alcon Inc., Fribourg (CH)

(72) Inventor: Zsolt Bor, San Clemente, CA (US)

(73) Assignee: Alcon Inc., Fribourg (CH)

( * ) Notice: Subject to any disclaimer, the term of this patent is extended or adjusted under 35 U.S.C. 154(b) by 606 days.

(21) Appl. No.: 17/937,986

(22) Filed: Oct. 4, 2022

(65) Prior Publication Data

US 2023/0157890 A1    May 25, 2023

Related U.S. Application Data

(60) Provisional application No. 63/281,271, filed on Nov. 19, 2021.

(51) Int. Cl.
*A61F 9/009* (2006.01)
*A61F 9/008* (2006.01)

(52) U.S. Cl.
CPC .... *A61F 9/009* (2013.01); *A61F 2009/00872* (2013.01); *A61F 2009/00885* (2013.01)

(58) Field of Classification Search
CPC ........... A61F 9/009; A61F 2002/00872; A61F 2009/00885; A61F 9/00825; G02C 7/047; A61D 9/008
See application file for complete search history.

(56) References Cited

U.S. PATENT DOCUMENTS

| | | |
|---|---|---|
| 3,780,979 A | 12/1973 | De |
| 4,357,088 A | 11/1982 | Pomerantzeff |
| 5,312,396 A | 5/1994 | Feld |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Jihan, L., Xiaoju, A., & Yi, K. (2018). Efficacy and safety of yttrium-aluminium garnet (YAG) laser vitreolysis for vitreous floaters. Journal of International Medical Research, 46(11), 4465-4471. doi:https://doi.org/10.1177/0300060518794245 (Year: 2018).*

(Continued)

*Primary Examiner* — Benjamin J Klein
*Assistant Examiner* — Alisha J Sircar
(74) *Attorney, Agent, or Firm* — Patterson + Sheridan, LLP

(57) ABSTRACT

In certain embodiments, a surgical contact lens system for ophthalmic treatment with a laser beam includes a patient contact lens and a surgical contact lens. The patient contact lens reduces one or more refractive errors of the eye and has a concave surface and a convex surface. The concave surface is to be disposed outwardly from a cornea of an eye. The surgical contact lens has an eye end to be disposed outwardly from the convex surface of the patient contact lens. The surgical contact lens includes a frame and an optical component coupled to the frame. The patient contact lens reduces pressure from the surgical contact lens to reduce corneal folding of a posterior surface of the cornea. The optical component of the surgical contact lens and the patient contact lens transmit the laser beam to treat the eye.

18 Claims, 4 Drawing Sheets

(56) References Cited

U.S. PATENT DOCUMENTS

| | | | |
|---|---|---|---|
| 5,548,352 A * | 8/1996 | Dewey | G02C 7/04 |
| | | | 351/219 |
| 5,909,270 A | 6/1999 | Moser | |
| 6,142,630 A * | 11/2000 | Koester | A61F 9/009 |
| | | | 351/219 |
| 6,322,556 B1 | 11/2001 | Gwon | |
| 6,551,306 B1 * | 4/2003 | Carriazo | A61F 9/00802 |
| | | | 606/4 |
| 6,789,900 B2 | 9/2004 | Van De Velde | |
| 7,374,287 B2 | 5/2008 | Van De Velde | |
| 7,510,282 B2 | 3/2009 | Ueno | |
| 7,520,613 B2 | 4/2009 | Saito et al. | |
| 7,703,922 B2 | 4/2010 | Van De Velde | |
| 8,480,659 B2 | 7/2013 | Frey et al. | |
| 8,652,602 B1 | 2/2014 | Dolla | |
| 8,783,868 B2 | 7/2014 | Qiu | |
| 8,876,808 B2 | 11/2014 | Feklistov et al. | |
| 8,994,753 B2 | 3/2015 | Nakano | |
| 9,033,500 B2 | 5/2015 | Utsunomiya | |
| 9,603,519 B2 | 3/2017 | Bor et al. | |
| 9,675,243 B2 | 6/2017 | Sasak et al. | |
| 9,789,002 B2 | 10/2017 | Van De Velde | |
| 10,130,511 B2 | 11/2018 | Dantus | |
| 10,478,342 B2 | 11/2019 | Dick | |
| 10,555,835 B2 | 2/2020 | Schuele et al. | |
| 2007/0093796 A1 * | 4/2007 | Raksi | A61F 9/009 |
| | | | 606/10 |
| 2007/0258094 A1 | 11/2007 | Izatt et al. | |
| 2007/0291277 A1 | 12/2007 | Everett | |
| 2009/0069794 A1 * | 3/2009 | Kurtz | A61F 9/00825 |
| | | | 606/4 |
| 2009/0073384 A1 | 3/2009 | Warden | |
| 2009/0137989 A1 * | 5/2009 | Kataoka | A61F 9/009 |
| | | | 606/5 |
| 2009/0196477 A1 | 8/2009 | Cense et al. | |
| 2010/0022994 A1 * | 1/2010 | Frey | A61F 9/009 |
| | | | 606/4 |
| 2010/0123873 A1 | 5/2010 | Raymond | |
| 2010/0152847 A1 | 6/2010 | Padrick | |
| 2011/0022035 A1 * | 1/2011 | Porter | A61F 9/00825 |
| | | | 606/4 |
| 2011/0077557 A1 | 3/2011 | Wing et al. | |
| 2012/0281235 A1 | 11/2012 | Murata | |
| 2013/0131652 A1 | 5/2013 | Dick | |
| 2013/0173029 A1 | 7/2013 | Caldeira et al. | |
| 2014/0058367 A1 | 2/2014 | Dantus | |
| 2014/0216468 A1 * | 8/2014 | Goldshleger | A61F 9/009 |
| | | | 128/845 |
| 2014/0222050 A1 * | 8/2014 | Heitel | A61F 9/009 |
| | | | 606/166 |
| 2014/0257257 A1 * | 9/2014 | Grant | A61F 9/00825 |
| | | | 606/4 |
| 2014/0268036 A1 | 9/2014 | Ketterling et al. | |
| 2014/0276674 A1 | 9/2014 | Lee | |
| 2015/0190278 A1 | 7/2015 | Gooding | |
| 2015/0342782 A1 | 12/2015 | Mordaunt | |
| 2016/0058617 A1 | 3/2016 | Luttrull et al. | |
| 2016/0074214 A1 | 3/2016 | Palanker et al. | |
| 2016/0074221 A1 | 3/2016 | Tassignon et al. | |
| 2016/0166431 A1 | 6/2016 | Vogler et al. | |
| 2016/0227999 A1 | 8/2016 | An et al. | |
| 2016/0235588 A1 | 8/2016 | Hart et al. | |
| 2016/0256324 A1 | 9/2016 | Suzuki | |
| 2016/0278629 A1 | 9/2016 | Schuele | |
| 2016/0302969 A1 | 10/2016 | Yamamoto | |
| 2017/0181625 A1 | 6/2017 | Kawakami et al. | |
| 2017/0252213 A1 | 9/2017 | Furuuchi et al. | |
| 2017/0326003 A1 | 11/2017 | Schuele et al. | |
| 2018/0028354 A1 | 2/2018 | Heeren | |
| 2018/0028355 A1 | 2/2018 | Raksi | |
| 2018/0140257 A1 | 5/2018 | Govindjee et al. | |
| 2018/0206719 A1 | 7/2018 | Adler et al. | |
| 2018/0317767 A1 | 11/2018 | Ryan | |
| 2018/0353064 A1 | 12/2018 | Soetikno et al. | |

| | | | |
|---|---|---|---|
| 2018/0368915 A1 | 12/2018 | Xia et al. | |
| 2019/0159933 A1 | 5/2019 | Romano et al. | |
| 2019/0282403 A1 | 9/2019 | Barrett et al. | |
| 2019/0290124 A1 | 9/2019 | Laforest et al. | |
| 2019/0313903 A1 | 10/2019 | Mckinnon | |
| 2019/0365569 A1 | 12/2019 | Skovgaard et al. | |
| 2020/0016000 A1 * | 1/2020 | Raksi | A61F 9/0084 |
| 2020/0038241 A1 | 2/2020 | Wang et al. | |
| 2020/0060873 A1 | 2/2020 | Heeren | |
| 2020/0085292 A1 | 3/2020 | Fukuma et al. | |
| 2020/0129336 A1 | 4/2020 | Schuele et al. | |
| 2020/0130103 A1 | 4/2020 | Choi | |
| 2020/0192080 A1 | 6/2020 | Karam | |
| 2020/0196853 A1 | 6/2020 | Van Hemert et al. | |
| 2020/0273218 A1 | 8/2020 | Camino et al. | |
| 2020/0397289 A1 | 12/2020 | Ralston | |
| 2020/0400422 A1 | 12/2020 | Ralston | |
| 2021/0069524 A1 * | 3/2021 | Kubota | G02C 7/04 |
| 2021/0100450 A1 | 4/2021 | Amma | |
| 2021/0186753 A1 | 6/2021 | Al-Qaisi et al. | |
| 2021/0275009 A1 | 9/2021 | Yates | |
| 2021/0378507 A1 | 12/2021 | Wallace | |
| 2021/0386586 A1 | 12/2021 | Bor | |
| 2022/0012459 A1 | 1/2022 | Schwiegerling | |
| 2022/0031511 A1 | 2/2022 | Charles | |
| 2023/0157889 A1 | 5/2023 | Bor | |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |

(56)                    References Cited

FOREIGN PATENT DOCUMENTS

| WO | 2015171793 A1 | 11/2015 |
|----|---------------|---------|
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |
| WO | 2021066047 A1 | 4/2021 |
| WO | 2021092211 A1 | 5/2021 |
| WO | 2021183637 A1 | 9/2021 |
| WO | 2022149028 A1 | 7/2022 |
| WO | 2023089416 A1 | 5/2023 |
| WO | 2023089459 A1 | 5/2023 |
| WO | 2023097391 A1 | 6/2023 |

OTHER PUBLICATIONS

Jihan, L., Xiaoju, A., & Yi, K. (2018). Efficacy and safety of yttrium-aluminium garnet (YAG) laser vitreolysis for vitreous floaters. Journal of International Medical Research, 46(11), 4465-4471. doi:https://doi.org/10.1177/0300060518794245 (Year Published: 2018).*
Marsack, Jason "Incorporating Wavefront Error Correction in Contact Lenses." Contact Lens Spectrum, Sep. 1, 2012, clspectrum.com/issues/2012/september/incorporating-wavefront-error-correction-in-contact-lenses/#:~:text=By%20Jason%20Marsack%2C%20PhD,error%20correction%20in%20contact%20lenses (Year Published: 2012).*
Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.
Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.
ELLEX Website, Treatment Guidelines—Laser Floater Removal; 2016, Ellex Medical Pty Ltd. E&OE. VB0002E, downloaded Apr. 20, 2017.
Felix Sauvage et al: "Photoablation of Human Vitreous Opacities by Light—Induced Vapor Nanobubbles", ACS Nano, vol. 13, No. 7, Jul. 9, 2019, pp. 8401-8416.
Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.
Michael J. Escuti, et al., "Geometric-Phase Holograms", Optics & Photonics News, pp. 22-29, Feb. 2016.
Milston Rebecca et al: "Vitreous floaters: Etiology, diagnostics, and management", Survey of Ophthalmology, vol. 61, No. 2, Mar. 1, 2016, pp. 211-227.
Nicusor Iftimia et al: "Hybrid retinal imaginer using line-scanning laser ophthalmoscopy and spectral domain optical coherence tomography", Optics Express, vol. 14, No. 26, Dec. 22, 2006.
Reece Bergstrom, et al., Vitreous Floaters, National Center for Biotechnology Information, May 21, 2020, 4 pages, Bookshelf ID NBK470420, StatPearls Publishing LLC, online.
Wikipedia Encyclopedia, Floater, Wikipedia Encyclopedia, Mar. 29, 2021, online: https://en.wikipedia.org/wiki/rloater?wprov=sfti 1.
Zhang Yunbo et al: "Parallel large-range scanning confocal microscope based on a digital micromirror device", Optik vol. 124, No. 13 (2013), Aug. 4, 2012, pp. 1585-1588.
Adrian G.H. Podoleanu et al., Combined optical coherence tomograph and scanning laser ophthalmoscope mi nije dostupan besplatno., Electronics Letters, 34 (11), 1998.
Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.
D. H. Kelly, "Retinal Inhomogeneity. II. Spatial Summation," J. Opt. Soc. Am., pp. 114-119, vol. 1, No. 1 (Jan. 1984).
D. H. Kelly, "Retinal Inhomogeneity. III. Circular-Retina Theory," D.H. Kelly, J. Opt. Soc. Am., pp. 810-819, vol. 2, No. 6 (Jun. 1985).
D.H. Kelly, "Visual Processing of Moving Stimuli," J. Opt. Soc. Am., pp. 216-225, vol. 2, No. 2 (Feb. 1985).
D.H. Kelly,, "Motion and Vision. II. Stabilized Spatio-Temporal Threshold Surface," J. Opt. Soc. Am., pp. 1340-1349, vol. 69, No. 10 (Oct. 1979).
D.H.KELLY, "Retinal Inhomogeneity. I. Spatiotemporal Contrast Sensitivity," J. Opt. Sec. Am., pp. 107-113, vol. 1, No. 1 (Jan. 1984).
Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.
Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.
Damodaran et al., "Digital micromirror device based ophthalmoscope with concentric circle scanning", 2017, pp. 2766-2780, vol. 8, No. 5, Biomedical Optics Express.
Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.
Ginner et al., "Wide-Field OCT Angiography at 400 KHz Utilizing Spectral Splitting", Photonics, Oct. 23, 2014, pp. 369-379, vol. 1, No. 4.
Heidelberg Engineering Gmbh, "Spectralis. Hardware Operating Instructions," Version 001, Aug. 2007.
Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.
Hofer et al., "Dispersion encoded full range frequency domain optical coherence tomography", Jan. 5, 2009, pp. 7-24, vol. 17, No. 1, Optics Express, US.
Hofer et al., "Fast dispersion encoded full range optical coherence tomography for retinal imaging at 800 nm and 1060 nm", Mar. 1, 2010, pp. 4898-4919, vol. 18, No. 5, Optics Express.
Leitgeb et al., "Complex ambiguity-free Fourier domain optical coherence tomography through transverse scanning", 2007, pp. 3453-3455, vol. 32, Optics Letters.
Li et al., "DMD-based three-dimensional chromatic confocal microscopy", 2020, pp. 4349-4356, vol. 59, No. 14, Applied Optics.
Martial et al., "Programmable Illumination and High-Speed, Multi-Wavelength, Confocal Microscopy Using a Digital Micromirror", Aug. 2012, e43942, vol. 7, No. 8, Plos One.
Reznicek Lukas et al., "Wide-Field Megahertz OCT Imaging of Patients with Diabetic Retinopathy", Journal of Diabetes Research, 2015, 5 pages.
Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

(56)                References Cited

OTHER PUBLICATIONS

Sarunic et al., "Instantaneous complex conjugate resolved spectral domain and swept-source OCT using 3x3 fiber couplers", Feb. 2005, pp. 957-967, vol. 13, No. 3, Optics Express.
Shields et al., "Wide-angle Imaging of the Ocular Fundus", Review of the Ophthalmology, Feb. 15, 2003.
Singh, "Lasers Take Aim At Floaters", Ophthalmology Management, Jul. 1, 2019, pp. 38, 40-42, 59, vol. 23.
Singh, "Modern vitreolysis—YAG laser treatment now a real solution for the treatment of symptomatic floaters", Survey of Ophthalmology, Mar. 3, 2020, pp. 581-591, vol. 65, No. 5.
SunLED, NanoPoint-0201 Series LEDs, published Feb. 15, 2016, www.SunLEDusa.com.
Volk Optical, "Volk Idrees Mid-Vitreous Lens", Dec. 20, 2020, accessed on Dec. 20, 2020 from https://www.volk.com/ . . . s?pr_prod_strat=collection_fallback&pr_rec_pid=4513049018402&pr_ref_pid=4513048952866pr_seq=uniform.
Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&amp;amp;_sid=b50c0674famp;amp;amp;_ ss=i.
Wang et al., "In vivo full range complex Fourier domain optical coherence tomography", Jan. 30, 2007, 054103, vol. 90, Applied Physics Letters.
Wojtkowski et al., "Full range complex spectral optical coherence tomography technique in eye imaging", 2002, pp. 1415-1417, vol. 27, No. 16, Optics Letters.
Yasuno et al., "Simultaneous B—M-mode scanning method for real-time full-range Fourier domain optical coherence tomography", 2006, pp. 1861-1865, vol. 45, No. 8, Applied Optics.
Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.
Zhou et al., "Dual channel dual focus optical coherence tomography for imaging accommodation of the eye", May 25, 2009, pp. 8947-8955, vol. 17, No. 11, Optics Express.

* cited by examiner

CONCAVE
SURFACE
126

PATIENT
CONTACT LENS
120

128
CONVEX
SURFACE

SURGICAL
CONTACT
LENS
122

FRAME
132

OPTICAL COMPONENTS
130

OPERATOR
END
142

140
EYE END

134
FLANGE

124
OUTER
SURFACE

SURGICAL CONTACT LENS SYSTEM WITH A PATIENT CONTACT LENS

TECHNICAL FIELD

The present disclosure relates generally to surgical contact lenses, and more particularly to a surgical contact lens system with a patient contact lens and a method for using the system.

BACKGROUND

In ophthalmic laser surgery, a surgeon may direct a laser beam into the eye to treat the eye. For example, a laser beam may be directed into the vitreous to treat eye floaters. Eye floaters are clumps of collagen proteins that form in the vitreous. These clumps disturb vision with moving shadows and distortions. To treat eye floaters, the surgeon places a surgical contact lens onto the eye to direct the laser beam into the eye. The laser beam is used to disintegrate the floaters, thus improving vision.

BRIEF SUMMARY

In certain embodiments, a surgical contact lens system for ophthalmic treatment with a laser beam includes a patient contact lens and a surgical contact lens. The patient contact lens reduces one or more refractive error(s) of the eye. The patient contact lens has a concave surface and a convex surface. The concave surface is to be disposed outwardly from a cornea of an eye. The surgical contact lens has an eye end to be disposed outwardly from the convex surface of the patient contact lens. The surgical contact lens includes a frame and an optical component coupled to the frame. The patient contact lens reduces pressure from the surgical contact lens to reduce corneal folding of a posterior surface of the cornea. The optical component of the surgical contact lens and the patient contact lens transmit the laser beam to treat the eye.

Embodiments may include none, one, some, or all of the following features:

The patient contact lens reduces corneal folding of the posterior surface of the cornea such that wavefront error of the laser beam is reduced.

The patient contact lens reduces refractive error(s) of the eye such that wavefront error of the laser beam is reduced.

A refractive error is an astigmatism.

The patient contact lens includes a hydrogel, silicone, silicone hydrogel, or polymethyl methacrylate (PMMA) material.

The patient contact lens is a hydrogel contact lens, a silicone hydrogel contact lens, a gas permeable (GP) lens, a rigid gas permeable (RGP) lens, a scleral contact lens, a hybrid contact lens, or a polymethyl methacrylate (PMMA) lens.

The eye end of the surgical contact lens is to be disposed outwardly from a contact gel that is disposed between the convex surface of the patient contact lens and the eye end of the surgical contact lens.

The surgical contact lens is an ocular Karickhoff four mirror lens, an ocular Karickhoff off-axis lens, an ocular Peyman lens, or a Singh mid-vitreous lens.

The optical component of the surgical contact lens and the patient contact lens transmit the laser beam to irradiate a floater in a vitreous of the eye.

The surgical contact lens is hand-held.

In certain embodiments, a method for using a surgical contact lens system for ophthalmic treatment with a laser beam includes disposing a patient contact lens outwardly from a cornea of an eye. The patient contact lens is designed to reduce one or more refractive error(s) of the eye and has a concave surface and a convex surface, where the concave surface is to be disposed outwardly from the eye. A surgical contact lens is disposed outwardly from the patient contact lens. The surgical contact lens has an eye end to be disposed outwardly from the convex surface of the patient contact lens. The surgical contact lens comprises an optical component coupled to a frame. The patient contact lens reduces force from the surgical contact lens in order to reduce corneal folding of a posterior surface of the cornea. The laser beam is directed through the optical component of the surgical contact lens and the patient contact lens to treat the eye.

Embodiments may include none, one, some, or all of the following features:

The method further includes reducing, by the patient contact lens, the corneal folding of the posterior surface of the cornea such that wavefront error of the laser beam is reduced.

The method further includes reducing, by the patient contact lens, the refractive error(s) of the eye such that wavefront error of the laser beam is reduced.

A refractive error is an astigmatism.

The method further includes disposing a contact gel outwardly from the convex surface of the patient contact lens between the patient contact lens and the eye end of the surgical contact lens.

The method further includes irradiating a floater in a vitreous of the eye by transmitting the laser beam through the optical component of the surgical contact lens and the patient contact lens.

The surgical contact lens is disposed outwardly from the patient contact lens by hand.

In certain embodiments, a patient contact lens for ophthalmic treatment with a laser beam has a concave surface and a convex surface. The concave surface is to be disposed outwardly from a cornea of an eye. The convex surface is to be in contact with an eye end of a surgical contact lens. The surgical contact lens includes an optical component coupled to a frame of the surgical contact lens. The optical component transmits the laser beam to treat the eye. The patient contact lens reduces one or more refractive error(s) of the eye, reduces pressure from the surgical contact lens to reduce corneal folding of a posterior surface of the cornea, and transmits the laser beam to treat the eye.

Embodiments may include none, one, some, or all of the following features:

The patient contact lens reduces the corneal folding of the posterior surface of the cornea such that wavefront error of the laser beam is reduced.

The patient contact lens reduces the refractive error(s) of the eye such that wavefront error of the laser beam is reduced.

DESCRIPTION OF EXAMPLE EMBODIMENTS

Figure 1:
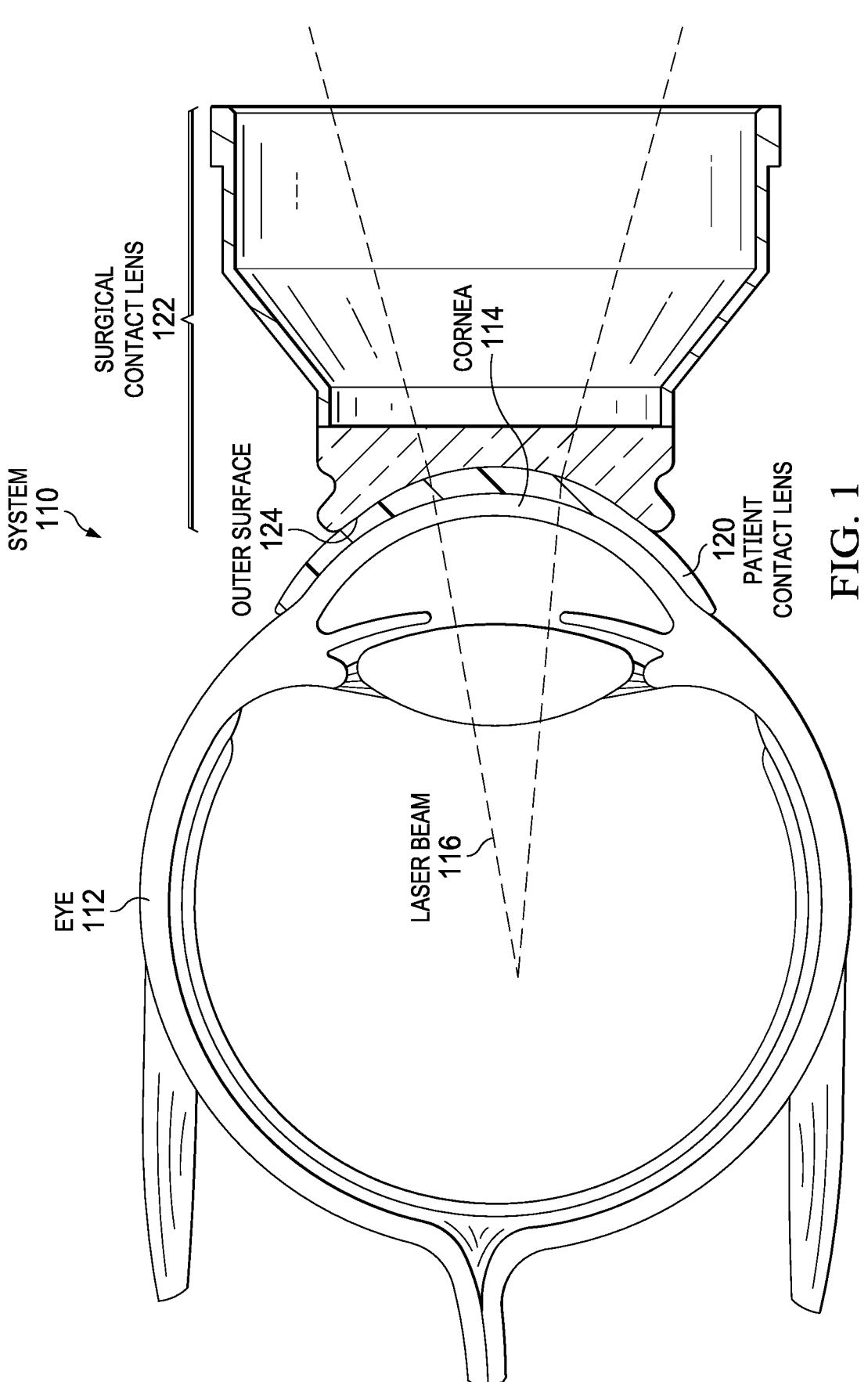
FIG. 1 illustrates an example of a surgical contact lens system that reduces laser beam wavefront errors, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Surgical contact lenses are important to direct the laser beam into the eye during surgery, but they can contribute to laser beam wavefront errors. Unknown to most people, surgical contact lenses create corneal folds in the eye, which contribute to wavefront errors. Wavefront errors undesirably increase the laser pulse energy needed to treat an eye (e.g., the energy needed to remove a floater from the eye). Accordingly, reducing wavefront errors lowers the needed pulse energy, which in turn improves retinal safety and treatment efficiency (e.g., floater disintegration efficiency). Improving efficiency decreases the number of pulses needed for treatment, thus reducing treatment time.

The surgical contact lens system disclosed herein includes a patient contact lens that reduces laser beam wavefront errors. The patient contact lens is disposed between the cornea and a surgical contact lens. The lens alleviates pressure on the cornea from the surgical contact lens, thus reducing corneal folds. The patient contact lens may also include corrective features that reduce the refractive error of the eye, further reducing wavefront errors. Thus, the surgical contact lens system reduces factors that degrade the laser beam, allowing for improved treatment of the eye.

FIG. 1 illustrates an example of a surgical contact lens system 110 that reduces laser beam wavefront errors, according to certain embodiments. Surgical contact lens system 110 includes a patient contact lens 120 disposed outwardly from cornea 114 of eye 112 and a surgical contact lens 122 disposed outwardly from patient contact lens 120. Laser beam 116 is transmitted through an optical component of surgical contact lens 122 and patient contact lens 120 to treat eye 112.

Patient contact lens 120 reduces corneal folding of a posterior surface of cornea 114 and refractive error of eye 12, which in turn reduces wavefront error of laser beam 116. Patient contact lens 120 is disposed between cornea 114 and outer surface 124 of surgical contact lens 122. The material of lens 120 alleviates pressure on cornea 114 by reducing and/or distributing the force of surgical contact lens 122 on cornea 114, which reduces corneal folding. Reducing corneal folding includes reducing folding to the extent that the folding is eliminated. Patient contact lens 120 may also have corrective features that reduce (or may even correct) refractive error of eye 12 when lens 120 is placed onto cornea 114. Reducing refractive error includes reducing error to the extent that the error is corrected.

Figure 2:
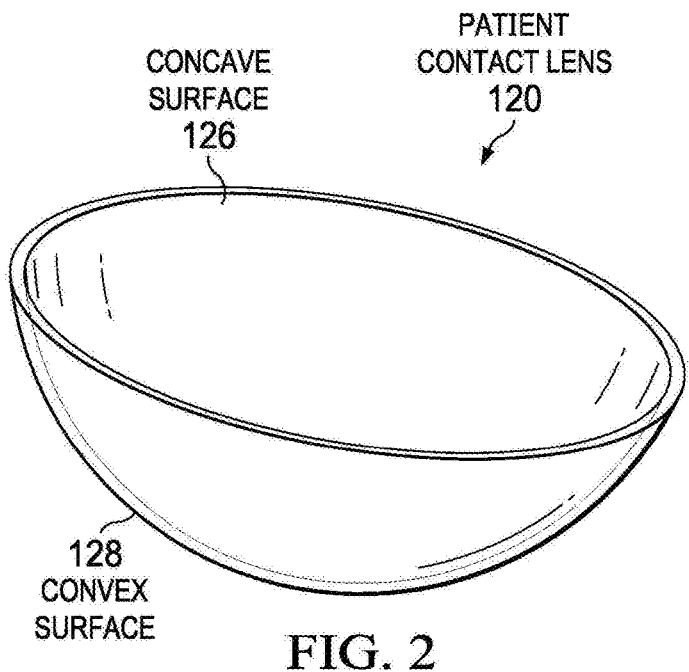
FIG. 2 illustrates an example of a patient contact lens that may be used with the surgical contact lens system of FIG. 1, according to certain embodiments.

FIG. 2 illustrates an example of patient contact lens 120 that may be used with surgical contact lens system 110 of FIG. 1, according to certain embodiments. Patient contact lens 120 has a concave surface 126 and a convex surface 128. Concave surface is configured to be disposed outwardly from cornea 114. Patient contact lens 120 may have corrective features (such as those of commercial corrective contact lenses) designed to reduce refractive error of the eye. Reducing a refractive error may range from decreasing the amount of error to substantially correcting the error. Patient contact lens 120 may reduce any suitable refractive error, such as a spherical error or higher order error, e.g., astigmatism. Patient contact lens 120 may also reduce corneal folding of cornea 114 by reducing and/or distributing the force of surgical contact lens 122 on cornea 114. Reducing corneal folds may range from decreasing the height of or substantially eliminating the corneal folds that would have occurred in the absence of patient contact lens 120.

Patient contact lens 120 may have any suitable size that can be placed outwardly from cornea 114. In certain embodiments, patient contact lens 120 may be slightly larger (e.g., a diameter greater by up to, e.g., 5 mm) than the outer diameter of surgical contact lens 122 such that lens 120 may be disposed between cornea 114 and surgical contact lens 122 to protect cornea 114 from the pressure of surgical contact lens 122. In other embodiments, patient contact lens 120 may be the same size as or slightly smaller (e.g., a diameter less than by up to, e.g., 5 mm) than the outer diameter of surgical contact lens 122.

Patient contact lens 120 may comprise any suitable material, such as a rigid material that can reduce and/or distribute the force of surgical contact lens 122 on cornea 114. Examples of suitable material include hydrogel, silicone, silicone hydrogel, and/or polymethyl methacrylate (PMMA). Examples of lens 120 include a hydrogel contact lens, silicone hydrogel contact lens, gas permeable (GP) lens, rigid gas permeable (RGP) lens, scleral contact lens, hybrid contact lens (a lens with a rigid GP central region surrounded by an outer region of hydrogel or silicone hydrogel material), and polymethyl methacrylate (PMMA) lens.

Figure 3:
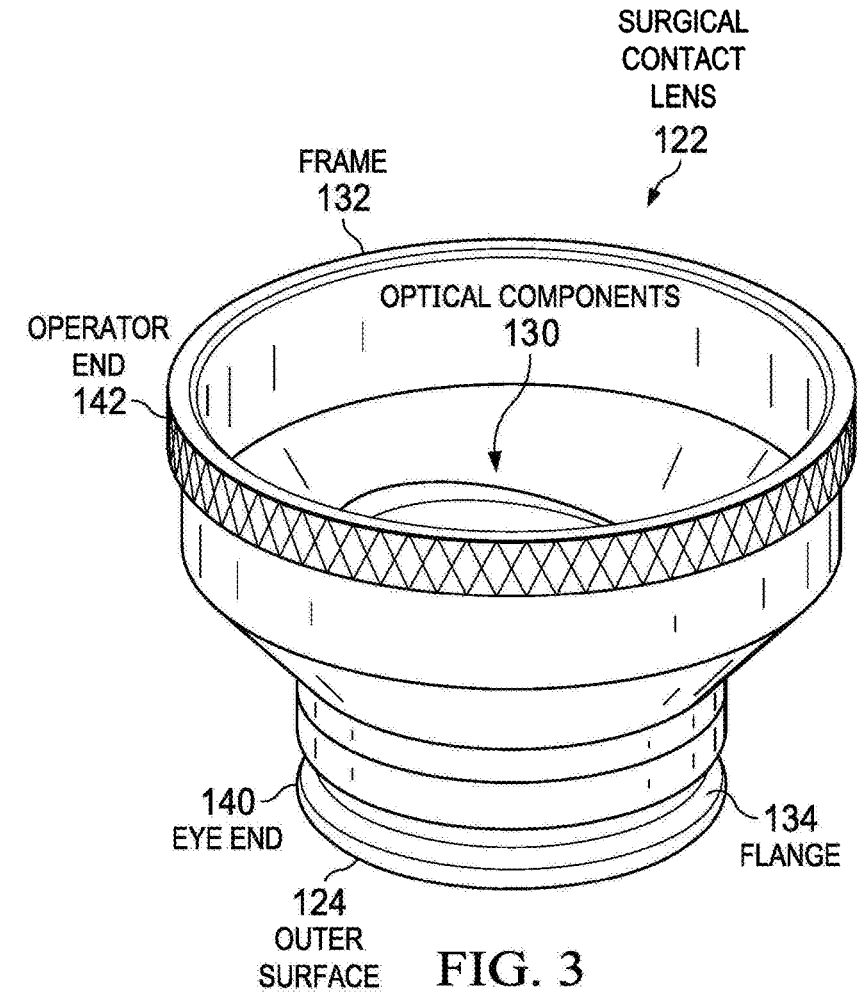
FIG. 3 illustrates an example of a surgical contact lens that may be used with the surgical contact lens system of FIG. 1, according to certain embodiments.

FIG. 3 illustrates an example of surgical contact lens 122 that may be used with surgical contact lens system 110 of FIG. 1, according to certain embodiments. Surgical contact lens 122 has an eye end 140 and an operator end 142. Eye end 140 is to be disposed outwardly from eye 112 and has a flange 134 that may be sized in the range of the average cornea +/−5 mm. Operator end 142 is to be handled by an operator such as a surgeon, and may have texture that allows the operator to easily handle end 142. Surgical contact lens 122 includes one or more optical components 130 and a frame 132, which has an annular shape.

Optical components 130 are coupled to and may be disposed within frame 132, and serve to magnify and/or focus the interior of eye 112. In general, an optical component transmits, refracts, reflects, or otherwise modulates light. In certain embodiments, optical components 130 include lens(es) and/or mirror(s) magnify and/or focus the interior of eye 112. In certain embodiments, outer surface 124 of optical components 130 has a curvature slightly less than that of the cornea, e.g., the radius of curvature may be 0 to 5 millimeters (mm) greater than that of the cornea, which may be approximately 7 mm.

Examples of surgical contact lens 122 include a Karickhoff four mirror lens, Karickhoff off-axis lens, Peyman lens, Sing mid-vitreous lens, and other frames with optical components that allow an operator to view an eye. For example, an ocular Karickhoff four mirror lens has four mirrors and a central axis view, which provides a view of the interior of the eye. As another example, an ocular Karickhoff off-axis lens has an off-axis view, which allows the operator to rotate the lens to view off-axis regions of the eye, without patient moving their eye. The focus point may allow for monitoring of the retina during treatment. As another example, an ocular Peyman lens may include lenses with focal points that treat different regions of the eye, e.g., the anterior chamber to the posterior capsule, mid-vitreous, and deep vitreous. As another example, a Singh mid-vitreous lens may provide views from the lens posterior to the retina.

In certain embodiments, a contact gel (e.g., a bubble-free optically-homogeneous contact gel) may be applied to patient contact lens 120 to accommodate surgical contact lens 122 and to allow for a better optical connection between patient contact lens 120 and surgical contact lens 122. In the embodiments, eye end 140 of surgical contact lens 122 is configured to be disposed outwardly from the contact gel applied to patient contact lens 120.

Figure 4:
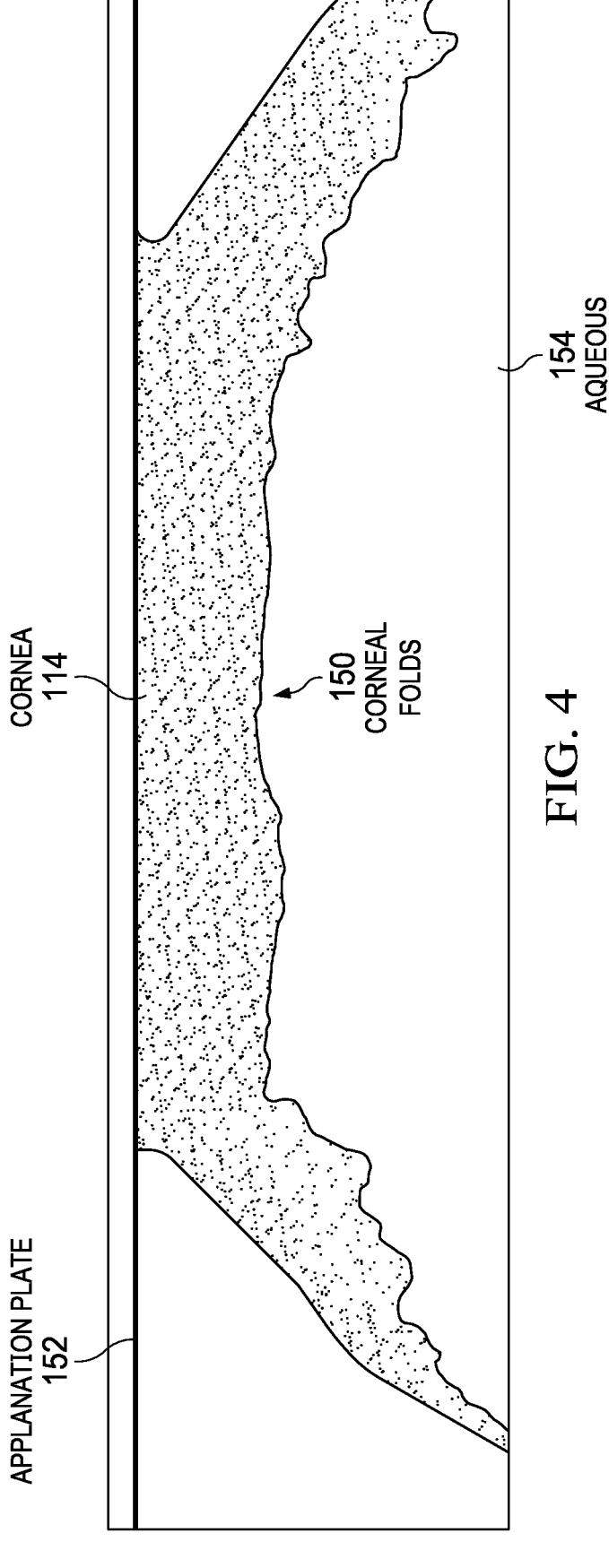
FIG. 4 illustrates an example of corneal folds.

FIG. 4 illustrates examples of corneal folds 150 that may be caused by an applanation plate 152 of certain known surgical contact lens systems. In general, corneal folds 150 are only detectable with highly sensitive imaging systems (e.g., OCT systems), so most people in the field fail to realize that folds 150 exist.

The different refractive indices of the cornea 114 and aqueous 154 cause the corneal folds 150 to yield significant wavefront errors of a laser beam. The corneal refractive index is 1.376, and the aqueous refractive index is 1.336, so the difference in refractive indices is 1.376−1.336=0.04. The RMS wavefront error may be determined according to H μm×0.04=0.04 H=0.04 H $\lambda$, where H represents the height of the corneal folds 150. In some cases, the height H of corneal folds 150 may be as high as 100 μm. An RMS wavefront error reduces the Strehl ratio, which is the ratio of peak intensities in the focal point with an aberrated and perfect phase front. For example, an RMS wavefront error of 0.13 $\lambda$ reduces the Strehl ratio from 1 to 0.5, that is, reduces the intensity of the focal point to 50%.

Figure 5:
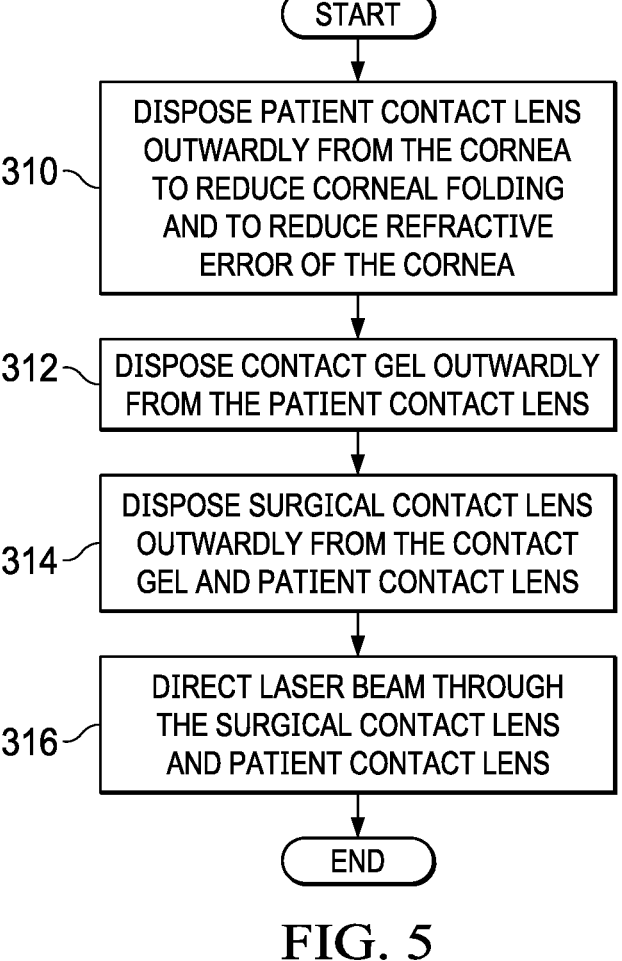
FIG. 5 illustrates an example of a method that may be used with the surgical contact lens system of FIG. 1 to reduce laser beam wavefront errors, according to certain embodiments.

FIG. 5 illustrates an example of a method that may be used with surgical contact lens system 110 of FIG. 1 to reduce laser beam wavefront errors, according to certain embodiments. The method starts at step 310, where a patient contact lens is disposed outwardly from the cornea. The patient contact lens is designed to reduce corneal folding and to reduce refractive error of the cornea, which in turn reduce wavefront errors of the laser beam. Contact gel is disposed outwardly from the patient contact lens at step 312 to allow for a better optical connection between the patient contact lens and surgical contact lens.

A surgical contact lens is disposed outwardly from the contact gel and patient contact lens at step 314. The surgical contact lens includes an optical component coupled to a frame. In certain embodiments, the patient contact lens alleviates pressure on the cornea by reducing and/or distributing the force of the surgical contact lens on the cornea, which reduces corneal folds and laser beam wavefront errors. A laser beam is directed through the optical component and patient contact lens to treat the eye at step 316. In certain embodiments, the laser beam is used to perform laser vitreolysis to remove floaters from the eye. The laser beam irradiates the floater to fragment, disintegrate, and/or remove the floater.

Although this disclosure has been described in terms of certain embodiments, modifications (such as changes, substitutions, additions, omissions, and/or other modifications)

of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A surgical contact lens system for ophthalmic treatment with a laser beam, comprising:
   a patient contact lens designed to reduce refractive errors of an eye including a spherical error of the eye and an astigmatism of the eye, the patient contact lens having a concave surface and a convex surface, the concave surface configured to be disposed outwardly from a cornea of an eye; and
   a surgical contact lens having an eye end configured to be disposed outwardly from the convex surface of the patient contact lens and comprising:
   a frame; and
   an optical component coupled to the frame,
   the patient contact lens configured to reduce pressure from the surgical contact lens to reduce corneal folding of a posterior surface of the cornea, the optical component of the surgical contact lens and the patient contact lens configured to transmit the laser beam to treat the eye.

2. The surgical contact lens system of claim 1, the patient contact lens configured to reduce the corneal folding of the posterior surface of the cornea such that wavefront error of the laser beam is reduced.

3. The surgical contact lens system of claim 1, the patient contact lens designed to reduce the refractive errors of the eye such that wavefront error of the laser beam is reduced.

4. The surgical contact lens system of claim 1, the patient contact lens comprising a material selected from hydrogel, silicone, silicone hydrogel, or polymethyl methacrylate (PMMA).

5. The surgical contact lens system of claim 1, the patient contact lens comprising a lens selected from a hydrogel contact lens, a silicone hydrogel contact lens, a gas permeable (GP) lens, a rigid gas permeable (RGP) lens, a scleral contact lens, a hybrid contact lens, or a polymethyl methacrylate (PMMA) lens.

6. The surgical contact lens system of claim 1, the eye end of the surgical contact lens configured to be disposed outwardly from a contact gel disposed between the convex surface of the patient contact lens and the eye end of the surgical contact lens.

7. The surgical contact lens system of claim 1, the surgical contact lens comprising a lens selected from an ocular Karickhoff four mirror lens, an ocular Karickhoff off-axis lens, an ocular Peyman lens, or a Singh mid-vitreous lens.

8. The surgical contact lens system of claim 1, the optical component of the surgical contact lens and the patient contact lens configured to transmit the laser beam to irradiate a floater in a vitreous of the eye.

9. The surgical contact lens system of claim 1, the surgical contact lens being hand-held.

10. A method for using a surgical contact lens system for ophthalmic treatment with a laser beam, comprising:

disposing a patient contact lens outwardly from a cornea of an eye, the patient contact lens designed to reduce refractive errors of the eye including a spherical error of the eye and an astigmatism of the eye, the patient contact lens having a concave surface and a convex surface, the concave surface configured to be disposed outwardly from the eye;

disposing a surgical contact lens outwardly from the patient contact lens, the surgical contact lens comprising an optical component coupled to a frame, the surgical contact lens having an eye end configured to be disposed outwardly from the convex surface of the patient contact lens, the patient contact lens configured to reduce force from the surgical contact lens in order to reduce corneal folding of a posterior surface of the cornea; and directing the laser beam through the optical component of the surgical contact lens and the patient contact lens to treat the eye.

11. The method of claim 10, further comprising:

reducing, by the patient contact lens, the corneal folding of the posterior surface of the cornea such that wavefront error of the laser beam is reduced.

12. The method of claim 10, further comprising:

reducing, by the patient contact lens, the refractive errors of the eye such that wavefront error of the laser beam is reduced.

13. The method of claim 10, further comprising:

disposing a contact gel outwardly from the convex surface of the patient contact lens to dispose the contact gel between the patient contact lens and the eye end of the surgical contact lens.

14. The method of claim 10, further comprising:

irradiating a floater in a vitreous of the eye by transmitting the laser beam through the optical component of the surgical contact lens and the patient contact lens.

15. The method of claim 10, the disposing the surgical contact lens outwardly from the patient contact lens further comprising:

placing the surgical contact lens outwardly from the patient contact lens by hand.

16. A patient contact lens for ophthalmic treatment with a laser beam, comprising: the patient contact lens having:

a concave surface configured to be disposed outwardly from a cornea of an eye;

a convex surface configured to be in contact with an eye end of a surgical contact lens, the surgical contact lens comprising an optical component coupled to a frame, the optical component configured to transmit the laser beam to treat the eye, the patient contact lens configured to:

reduce refractive errors of the eye including a spherical error of the eye and an astigmatism of the eye;

reduce pressure from the surgical contact lens to reduce corneal folding of a posterior surface of the cornea; and transmit the laser beam to treat the eye.

17. The patient contact lens of claim 16, the patient contact lens configured to reduce the corneal folding of the posterior surface of the cornea such that wavefront error of the laser beam is reduced.

18. The patient contact lens of claim 16, the patient contact lens designed to reduce the refractive errors of the eye such that wavefront error of the laser beam is reduced.

\* \* \* \* \*